United States Patent
Streppel et al.

(10) Patent No.: US 8,886,472 B2
(45) Date of Patent: *Nov. 11, 2014

(54) METHOD FOR DETERMINING A CONDITION INDICATOR OF AN APPARATUS

(71) Applicants: Toon Streppel, AG Eerbeek (NL); Torsten Seehaus, Duesseldorf (DE); Ulrich Schmitz, Kerken (DE); Manfred Battefeld, Duesseldorf (DE); Frank Thomas, Solingen (DE); Michael Kussmann, Duesseldorf (DE); Michael Haeck, Bergisch Gladbach (DE)

(72) Inventors: Toon Streppel, AG Eerbeek (NL); Torsten Seehaus, Duesseldorf (DE); Ulrich Schmitz, Kerken (DE); Manfred Battefeld, Duesseldorf (DE); Frank Thomas, Solingen (DE); Michael Kussmann, Duesseldorf (DE); Michael Haeck, Bergisch Gladbach (DE)

(73) Assignee: Hach Lange GmbH, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/920,101

(22) Filed: Jun. 18, 2013

(65) Prior Publication Data

US 2013/0282303 A1    Oct. 24, 2013

Related U.S. Application Data

(63) Continuation of application No. 12/718,164, filed on Mar. 5, 2010, now Pat. No. 8,510,064.

(30) Foreign Application Priority Data

Mar. 6, 2009  (EP) .................................. 09154512

(51) Int. Cl.
*G01N 33/00* (2006.01)
*G01N 33/18* (2006.01)

(52) U.S. Cl.
CPC ............ *G01N 33/18* (2013.01); *G01N 33/1886* (2013.01)
USPC .............................................. 702/50; 702/30

(58) Field of Classification Search
USPC ......... 702/22, 27, 28, 30, 32, 50; 436/73, 177
See application file for complete search history.

(56) References Cited

U.S. PATENT DOCUMENTS

| | | | |
|---|---|---|---|
| 6,392,416 B1 | 5/2002 | Keech | |
| 8,510,064 B2 * | 8/2013 | Streppel et al. | 702/50 |
| 2002/0145417 A1 | 10/2002 | Brockhaus | |

FOREIGN PATENT DOCUMENTS

| | | |
|---|---|---|
| DE | 101 18 003 A1 | 10/2002 |
| WO | WO 99/34174 A1 | 7/1999 |

* cited by examiner

*Primary Examiner* — Manuel L Barbee
(74) *Attorney, Agent, or Firm* — Norman B. Thot

(57) ABSTRACT

A method for determining a condition indicator of an apparatus includes providing an apparatus configured to measure at least two different technical parameters. A respective parameter value is determined for each of the at least two different technical parameters of the apparatus using at least one sensor configured to determine a respective parameter value for each of the at least two different technical parameters. A respective deviation value is determined for each of the parameter values with respect to an associated respective parameter reference value for each of the technical parameters. A respective deviation relevance value is determined from each of the deviation values using a respective parameter-specific deviation relevance function for each of the parameter values, the parameter-specific deviation relevance functions being different from each other. Using an indicator function, a condition indicator is calculated from the determined deviation relevance values. An overall condition of the apparatus is determined using the condition indicator.

11 Claims, 1 Drawing Sheet

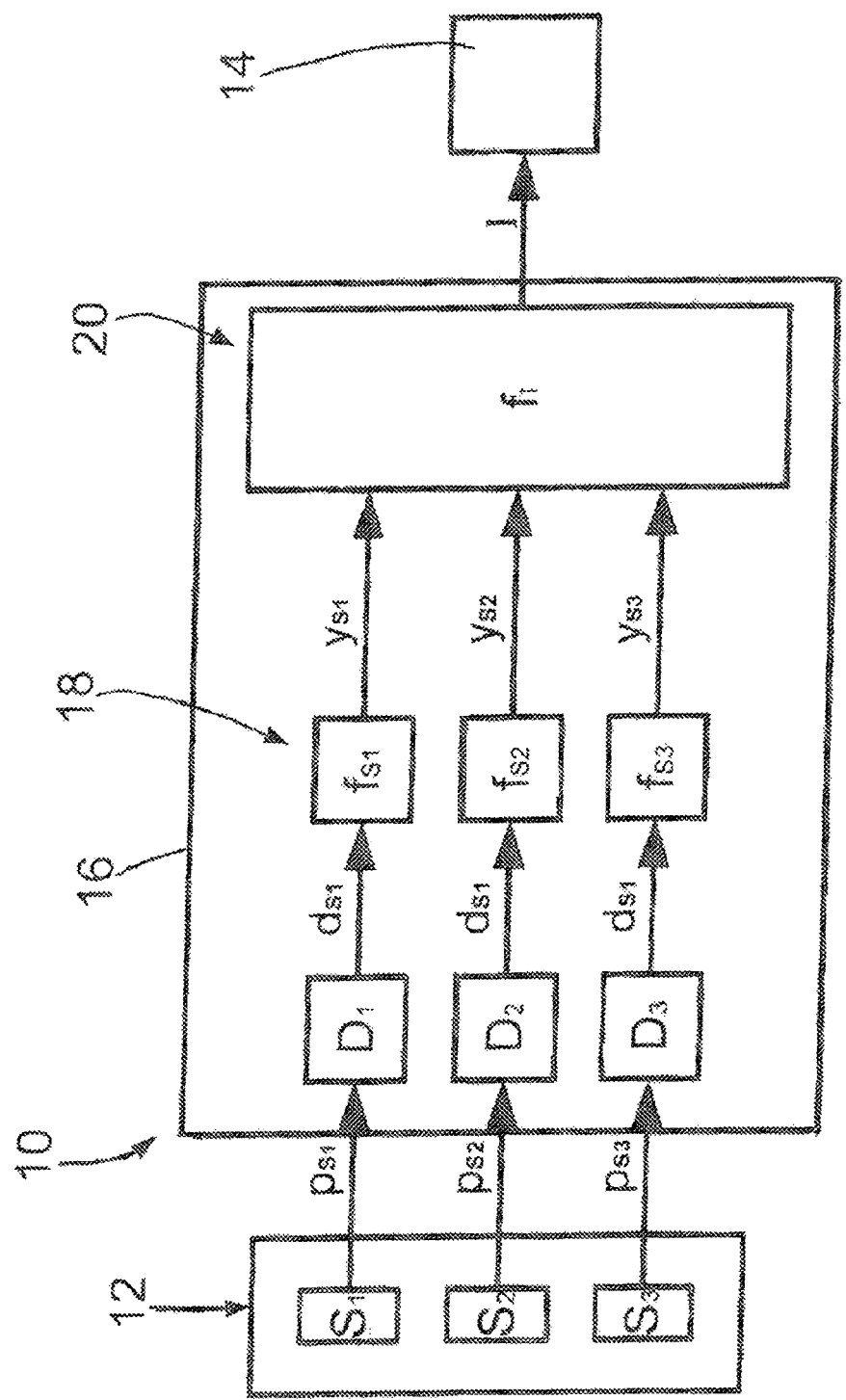

METHOD FOR DETERMINING A CONDITION INDICATOR OF AN APPARATUS

CROSS REFERENCE TO PRIOR APPLICATIONS

This application is a continuation of application Ser. No. 12/718,164, filed on Mar. 5, 2010. Application Ser. No. 12/718,164 claimed priority to European Patent Application No. EP 09154512.9-1240, filed Mar. 6, 2009. The entire disclosure of said application is incorporated by reference herein.

FIELD

The present invention relates to a method for determining a condition indicator of an apparatus.

BACKGROUND

Apparatuses are used, for example, for a qualitative and quantitative determination of one or more analytes in water, such as in waste water or drinking water. Apparatuses may be configured as so-called laboratory apparatuses for individual measuring or as process apparatuses for quasi-continuous measuring.

Prior art apparatuses provide no or only insufficient information about the technical condition of the analysis apparatus so that it is not readily possible to judge the state of health of the analysis apparatus or the trustworthiness of the measured values supplied by the analysis apparatus.

SUMMARY

An aspect of the present invention is to provide an apparatus which supplies information on the overall condition of the analysis apparatus in the form of a condition indicator.

In an embodiment, the present invention provides a method for determining a condition indicator of an apparatus which includes providing an apparatus configured to measure at least two different technical parameters. A respective parameter value is determined for each of the at least two different technical parameters of the apparatus using at least one sensor configured to determine a respective parameter value for each of the at least two different technical parameters. A respective deviation value is determined for each of the parameter values with respect to an associated respective parameter reference value for each of the technical parameters. A respective deviation relevance value is determined from each of the deviation values using a respective parameter-specific deviation relevance function for each of the parameter values, the parameter-specific deviation relevance functions being different from each other. Using an indicator function, a condition indicator is calculated from the determined deviation relevance values. An overall condition of the apparatus is determined using the condition indicator.

BRIEF DESCRIPTION OF THE DRAWINGS

The present invention is described in greater detail below on the basis of embodiments and of the drawing in which:

FIG. 1 schematically illustrates an apparatus in which a method for determining a condition indicator is implemented.

DETAILED DESCRIPTION

According to the method of the present invention, the following method steps are provided for the determination of a condition indicator of an analysis apparatus:

determining one respective parameter value for at least two different technical parameters of the apparatus;

determining a value of deviation of the parameter value with respect to an associated parameter reference value for all parameters, respectively;

determining one respective deviation relevance value from the deviation value using a parameter-specific deviation relevance function for all parameters, respectively, the functions being different from each other; and calculating the condition indicator from all deviation relevance values determined using an indicator function.

First, corresponding parameter values are determined for several technical parameters of the analysis apparatus, for example, an air humidity value can be determined by an air humidity sensor in the analysis apparatus, or a power consumption value of a photometric radiation source, a position value of a wiper, a counter value of a wiper oscillation counter, etc. may be determined.

Thereafter, a relative or absolute deviation value can be determined for each determined parameter value with respect to an associated parameter reference value. The reference value may, for example, be an ideal value for the respective parameter. The deviation value indicates an absolute or relative deviation of the parameter value from the reference value. The deviation value itself does not give an immediate indication of the degree of relevance of the deviation from the ideal value for the functionality of the analysis apparatus or for the quality of the measured value.

After the deviation value has been determined for all relevant parameters, a deviation relevance value can be determined for each parameter using a respective parameter-specific function. With at least two parameters, the functions for each of these two parameters should be different from each other. This function establishes a relation between the deviation value and its relevance with respect to the functionality of the analysis apparatus or to the quality of the measured values. For example, a slight deviation of the air humidity value from an ideal value in a housing of the analysis apparatus can generate a deviation relevance value of 1.0, whereas a substantially greater deviation may suddenly result in a deviation relevance value of 0.3. The same can be true for the power consumption of a brightness-controlled photometric light source, for example, which will cause a dramatic change in the deviation relevance value when a threshold is reached. With a wiper, which is to wipe a measuring window clean from residues before each analysis, for example, the blocking of only a single wiper oscillation may result in an unchanged deviation relevance value of 1.0, for example, if the attempted wiping can be successfully repeated immediately after the blocking. If a blocking also occurs at the repeated attempt, the deviation relevance value may, for example, decrease to 0.8. In the examples described, a deviation relevance value of 1.0 characterizes an optimal condition and a value of 0.0 characterizes a very poor condition.

Finally, an indicator function can be used to calculate a condition indicator from the deviation relevance values of the relevant parameters, which indicator may, for example, be an apparatus condition indicator or a measured value quality indicator. The indicator function for determining the apparatus condition indicator may differ substantially with respect to the importance of the parameter "air humidity" from the indicator function for determining the measured value quality indicator. A high air humidity in the housing of the analysis apparatus may, for example, be important for the apparatus condition indicator since it would hint at a leak in the housing, whereas it is of only minor importance for the measuring quality parameter since it has no immediate influence on the reliability of a measured value.

Using the above described method, a condition indicator for the analysis apparatus can be generated that represents significant information about a certain aspect of the measuring apparatus. The condition indicator provides even an untrained and inexperienced user with information on a certain aspect of the analysis apparatus without requiring a complex expert's knowledge.

The indicator function can include, for example, a term for the arithmetic mean of a plurality of deviation relevance values. For example, the indicator function can include a term containing a multiplication of the smallest of all deviation relevance values by the arithmetic mean of all other deviation relevance values.

In an embodiment of the present invention, a parameter is determined by a reagent quantity sensor in a reservoir, a humidity sensor in the apparatus housing, a motor current sensor of a drive motor, a power sensor of a photometer light source, a wiper blade oscillation counter, a wiper blade blocking sensor, a wiper blade position sensor and/or a drive motor rotation counter.

In an embodiment of the present invention shown in FIG. 1, the apparatus 10 is a process analysis apparatus designed as an immersion probe. The analysis apparatus 10 comprises a sensor unit 12 in which a plurality of sensors S1, S2, S3 are arranged.

The sensor S1 is a humidity sensor in the housing of the sensor unit 12 that measures the air humidity within the sensor unit housing which, in operation, is immersed in water. If the air humidity within the housing exceeds a certain limit value, a leak in the housing can be assumed which, in the long run, could lead to substantial trouble and damage of the sensor unit 12 or the analysis apparatus 10. The air humidity determined by the humidity sensor thus is a parameter that is substantially included in a statement on the condition of the apparatus.

The sensor S2 is a wiper position sensor that indicates the wiper position of a wiper wiping the sensor window of the sensor unit 12. The wiper position sensor may either determine the exact position of the wiper or the presence of the wiper at a certain position. Using the wiper position sensor, it can be determined whether the wiper is blocked, and the number of wiping oscillations can be counted in combination with a corresponding counter. Since the effective wiping of the measuring window by the wiper influences the quality of the measurement result, information about a wiper blocking or the wear of the wiper are relevant for an overall statement on the measured value quality.

The sensor S3 is a light source power sensor that indicates the electric power requirement of a brightness-controlled photometer light source. Every light source, even a LED, ages due to operation. Age often shows in particular that, based on a constant light output, more electric power is needed for an older light source than was required for the light source when new. With the change in power requirement, the emitted spectrum of the light source may change as well whereby the measured value quality can be impaired. The information supplied by the light source power sensor can thus be included in particular in the apparatus condition, but may also be included in the measured value quantity.

Further sensors provided may include reagent quantity sensors detecting the level of the respective reagents in corresponding reservoirs. Further, the drive motor of the wiper may be provided with a sensor counting the number of rotations of the motor, thereby indirectly measuring the wear of the motor. A motor current sensor can provide more information about the drive motor and/or the wiper. The motor current sensor may also serve as a wiper blocking sensor with which the blocking of the wiper can be detected. Basically, information from any kind of sensor of the analysis apparatus can be included in the determination of a measured value quality indicator and/or a housing condition indicator.

The parameter values $p_{S1}$, $p_{S2}$, $p_{S3}$ determined by the sensors $S_1$, $S_2$, $S_3$ are supplied to a microprocessor 16 and compared with a parameter reference value in computing modules $D_1$, $D_2$, $D_3$. The comparison is effected by calculating the difference from the respective parameter reference value or by division by the respective parameter reference value. In this manner, a deviation value $d_{S1}$, $d_{S2}$, $d_{S3}$ can be determined for each sensor $S_1$, $S_2$, $S_3$ or each parameter, which deviation value is supplied to a second stage of computing modules.

In the example of an air humidity sensor supplying a relative air humidity value, the reference value may, for example, be an ideal value of 0% air humidity. Determining a deviation value may be effected by calculating the difference or by division. The deviation value can, for example, be determined from the quotient of the difference between the parameter value and the reference value as the numerator and the reference value as the denominator.

In the example of a wiper position sensor supplying information on wiper blockings, the reference value may, for example, be 4. The deviation value may then result from the number of the actual wiping cycles with respect to the last 4 wiping cycle attempts and thus yield a value between 4/4 and 0/4.

In the second computing modules 18, a deviation relevance value $y_{S1}$, $y_{S2}$, $y_{S3}$ can be determined for each parameter from the deviation values $d_{S1}$, $d_{S2}$, $d_{S3}$ using a parameter-specific deviation relevance function $f_{S1}$, $f_{S2}$, $f_{S3}$. Due to the deviation relevance function, in particular small negligible deviations from an ideal value or large deviations from a limit value can be rated as having very little relevance. Generally, the deviation relevance function is different for each parameter and may, for example, indicate the deviation relevance value in a range from 0.1 to 1.0, where a value of 1.0 indicates the ideal condition and 0.0 indicates a very poor condition.

The condition indicator I is individualized in particular in the computing modules 18. If several different condition indicators I are to be determined for the same analysis apparatus 10, the process before the computing modules 18 splits into two or more branches in which, in particular, the respective deviation relevance functions $f_{S1}$, $f_{S2}$, $f_{S3}$ differ from each other.

The indicator function $f_I$ may, for example, be a polynomial in which the deviation relevance values are given factors of different sizes. An apparatus condition indicator or a measured value quality indicator can, for example, be generated as a condition indicator. Whereas the air humidity and the number of rotations of the motor, for example, are relevant in the indicator function for the apparatus condition, they can be ignored, in relative terms, in the indicator function for the measured value quality.

The indicator function $f_I$ can, for example, be a multiplication of the smallest deviation relevance value $y_{S1}$, $y_{S2}$, $y_{S3}$ by the arithmetic mean of the other deviation relevance value $y_{S1}$, $y_{S2}$, $y_{S3}$.

The condition indicator I can, therefore, be outputted to a display 14 or to a computer for a further processing of the condition indicator I. If need be, the computer may effect corresponding measures in the analysis apparatus if the condition indicator I exceeds a limit value.

The indicator function may, for example, take the following form:

$$I = \min f_{Si} \times (\Sigma f_{Si} - \min f_{Si})/(\max(i)-1)$$

where $f_{Si}$ is the respective deviation relevance function $f_{S1}$-$f_{S3}$.

A deviation relevance function $f_{Si}$ may, for example, take the following form:

$$f_{Si} = (1-\text{start}) \times (1-d_{Si})^n + \text{start}$$

where $d_{Si}$ is a deviation value $d_{S1}$, $d_{S2}$, $d_{S3}$ and the values "start" and n determine the form of the curve.

Although the present invention has been described and illustrated with reference to specific illustrative embodiments thereof, it is not intended that the present invention be limited to those illustrative embodiments. Those skilled in the art will recognize that variations and modifications can be made without departing from the true scope of the present invention as defined by the claims that follow. It is therefore intended to include within the present invention all such variations and modifications as fall within the scope of the appended claims and equivalents thereof.

What is claimed is:

1. An apparatus configured to measure at least two different technical parameters, the apparatus comprising:
    at least one sensor configured to determine a respective parameter value for each of the at least two different technical parameters; and
    a condition indicator configured to determine an overall condition of the apparatus by a method comprising:
        determining a respective parameter value for each of at least two different technical parameters of the apparatus;
        determining a respective deviation value for each of the parameter values with respect to an associated respective parameter reference value for each of the technical parameters;
        determining a respective deviation relevance value from each of the deviation values using a respective parameter-specific deviation relevance function for each of the parameter values, the parameter-specific deviation relevance functions being different from each other; and
        calculating, using an indicator function, the condition indicator for the apparatus from the determined deviation relevance values.

2. The apparatus as recited in claim 1, wherein the indicator function includes a term for an arithmetic mean of a plurality of the deviation relevance values.

3. The apparatus as recited in claim 2, wherein the term includes a multiplication of the smallest of the deviation relevance values by an arithmetic mean of other of the deviation relevance values.

4. The apparatus as recited in claim 1, wherein the condition indicator is an apparatus condition indicator.

5. The apparatus as recited in claim 1, wherein the condition indicator is a measured value quality indicator.

6. The apparatus as recited in claim 1, wherein the apparatus is at least one of a process analysis apparatus and a water analysis apparatus.

7. The apparatus as recited in claim 1, wherein a first of the parameter values is determined by a humidity sensor.

8. The apparatus as recited in claim 1, wherein a first of the parameter values is determined by a reagent quantity sensor.

9. The apparatus as recited in claim 1, wherein a first of the parameter values is the motor current of a drive motor.

10. The apparatus as recited in claim 9, wherein the drive motor is configured to drive a wiper for wiping a measurement window.

11. The apparatus as recited in claim 1, further comprising supplying the condition indicator to another apparatus component.

* * * * *